(12) United States Patent
Wu

(10) Patent No.: US 7,015,686 B1
(45) Date of Patent: Mar. 21, 2006

(54) TEST MECHANISM FOR TESTING CONNECTION PORT OF ELECTRONIC APPARATUS

(75) Inventor: Gordon Wu, Taipei (TW)

(73) Assignee: Inventec Corporation, Taipei (TW)

( * ) Notice: Subject to any disclaimer, the term of this patent is extended or adjusted under 35 U.S.C. 154(b) by 0 days.

(21) Appl. No.: 10/983,679

(22) Filed: Nov. 9, 2004

(51) Int. Cl.
*G01N 19/00* (2006.01)
*G01L 5/00* (2006.01)

(52) U.S. Cl. .............................. 324/158.1; 73/862.01; 73/865.9

(58) Field of Classification Search ..................... None
See application file for complete search history.

*Primary Examiner*—Paresh Patel
(74) *Attorney, Agent, or Firm*—Bacon & Thomas, PLLC

(57) ABSTRACT

The present invention is to provide a test mechanism for testing a connection port of an electronic apparatus comprising a support platform on which at least one slideway is disposed, two mobile grasping components mounted respectively on these slideways such that these grasping components are able to push against both sides and one corresponding surface of the electronic apparatus and fix the electronic apparatus onto the support platform, for testing and estimating whether the connection port with a load object connected thereto in various angles meets with anticipated quality requirement.

6 Claims, 3 Drawing Sheets

TEST MECHANISM FOR TESTING CONNECTION PORT OF ELECTRONIC APPARATUS

BACKGROUND OF THE INVENTION

1. Field of the Invention

The present invention relates to a test mechanism, more particularly to a test mechanism for testing a connection port of an electronic apparatus in order to estimate whether the connection port is able to bear with a load object connected thereto in various angles and meet with the anticipated quality requirement.

2. Prior Art

With gradual progress of science and technology, it may be said that commercial electronic apparatuses tend to get mature types and comprise everything that one expects to find day by day. For example, there are many kinds of mobile phone, digital camera, notebook computer, etc, which provide with powerful functions and exquisite appearances, and competitions among manufacturers are becoming more and more intense. As a result, various trade products that provide with warranties are now available in the market. Every manufacturer also demands more and more strict quality control for their products. No matter what kind of electronic product is provided, various connection ports, for example, a universal series bus (USB), a monitor-out port, an Internet connection port, etc, are usually mounted on side faces of the electronic product. Moreover, it is worthy to pay much attention to the quality issue to realize puling forces of the load object that the connection port of the electronic apparatus in various angles can bear with without fall.

As a result, there are more and more consumers want to know the load rotation lifetime of a connection port of an electronic apparatus, which load rotation indicates that a load object is connected to the connection port of the electronic product, and the electronic apparatus is further rotated for testing the connection port of the electronic apparatus in various angles to realize that whether the connection port is able to stand for the test and also estimate that whether the connection port is qualified. But, there is no commercial experimental machine that provides with this function since no similar test is previously disclosed. Nevertheless, there are various conventional test mechanism s at present that test various apparatuses particularly in a plug-in and plug-out manner. Even if it is different from the purpose of testing the load rotation lifetime of the connection port of the electronic apparatus that the consumers want to realize, they have something in common, wherein these two have differences in that test mechanism with the plug-in and plug-out manner is to test the number of times that the connection port of the electronic apparatus can be plugged in and out, which is adopted to determine whether the electronic apparatus is qualified or not; and the load rotation lifetime test of the connection port of the electronic apparatus is to test the load pulling force that the connection port of the electronic apparatus can bear with, which is also adopted to determine whether the electronic apparatus is qualified or not. Besides, these two are identical in that both of them want to realize that whether the electronic apparatus is durable and qualified in accordance with the test results.

Since these two have something in common and there is no commercial test mechanism that can be applied to test the load rotation lifetime of the connection port of the electronic apparatus, a test mechanism of the present invention is disclosed in view of this demand so as to satisfy the requirement of consumers.

SUMMARY OF THE INVENTION

The present invention has been accomplished in view of the aforementioned circumstances so as to enable consumer to test the load rotation lifetime of a connection port of an electronic apparatus for further realizing the load pulling force that the connection port of the electronic apparatus can bear with in various angles. As a result, the inventor has been made sustained researches and experiments to eventually develop a test mechanism for testing a connection port of an electronic apparatus of the present invention in accordance with the inventor's accumulated experience and skill in the art.

According to one aspect of the present invention, a test mechanism for testing a connection port of an electronic apparatus is provided for testing the load pulling force that the connection port of the electronic apparatus can bear with in various angles so as to estimate that whether the connection port of the electronic apparatus provides with anticipated quality requirement, wherein the manner of fixing the connection port of the electronic apparatus on the test mechanism is to provide with a support platform on which at least one slideway is disposed. Two mobile grasping components are mounted respectively on these slideways such that these grasping components are able to slide along the corresponding slideways and against both sides of the electronic apparatus while fixing the electronic apparatus onto the support platform. At this moment, a slide base provided on one end of each grasping component is fixed and locked on both sides of the electronic apparatus. Thereafter, a grasping member penetrates a grasping arm that is provided on the other end of each grasping component for pushing against one corresponding surface of the electronic apparatus. As a result, the electronic apparatus is firmly fixed on the support platform.

According to another aspect of the present invention, the support platform is disposed on the rotation shaft adjacent to the transmission control box in a position eccentric to the rotation shaft.

According to still another aspect of the present invention, the test mechanism utilizes a sensor to sense that whether the load object mounted on the connection port of the electronic apparatus falls or not. If the load object falls, the sensor transmits a signal to stop the test mechanism from performing experiment.

According to still another aspect of the present invention, in order to provide user with a test mechanism that can be operated easily and comprises several selectable action modes, a man-machine interface is disposed on one side of the test mechanism. As a result, the test mechanism is capable of using various rotation modes to test the connection port of the electronic apparatus by assigning various parameter values.

The above and other objects, features and advantages of the present invention will become apparent from the following detailed description taken with the accompanying drawings.

DETAILED DESCRIPTION OF THE PREFERRED EMBODIMENT

Figure 1:
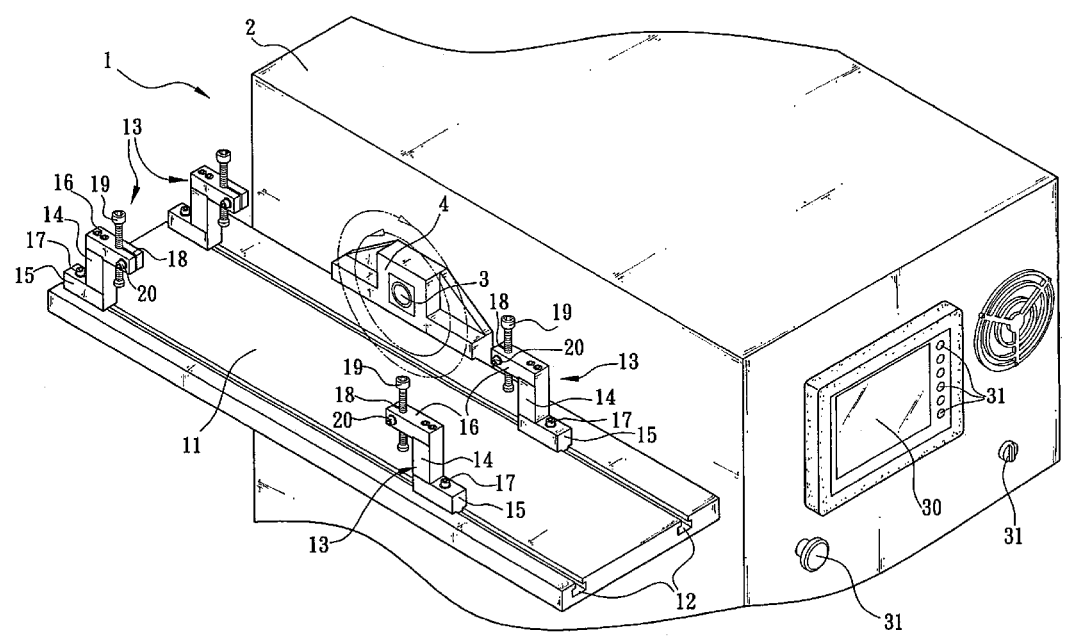
FIG. 1 is a schematic view of a test mechanism for testing a connection port of an electronic apparatus in accordance with the present invention.

As shown in FIG. 1, the present invention relates to a test mechanism for testing a connection port of an electronic apparatus on which a machine body 1 is disposed. The machine body 1 comprises a transmission control box 2 and a support platform 11. A rotation shaft 3 is mounted inside the transmission control box 2, wherein one end of the rotation shaft 3 extends from a surface of the transmission control box 2. Moreover, a connection piece 4 receives and connects to the end of the rotation shaft 3, which is extended from the transmission control box 2. One end of the connection piece 4 is connected to one side of the support platform 11, which is disposed on the rotation shaft 3 through the connection piece 4 adjacent to the transmission control box 2 in a position eccentric to the rotation shaft 3. As a result, because of the mounting relationship between the connection piece 4 and the support platform 11, the connection piece 4 drive and rotate the support platform 11 smoothly when the rotation shaft 3 is rotated.

According to the present invention, at least one slideway 12 is disposed on the support platform 11. Two mobile grasping components 13 are mounted respectively on these slideways 12. Each one of these grasping components 13 includes a main body 14. A slide base 15 is provided on one end of the main body 14 and slidablely inserted into the slideway 12. A grasping arm 16 is provided on the other end of the main body 14. The slide base 15 and the grasping arm 16 are arranged in opposite directions. As a result, the grasping component 13 is able to slide freely on the slideway 12 by means of the slide base 15.

Besides, please refer to FIG. 1 again, each slide base 15 comprises a regulating button 17 for fixing up these grasping components 13 on the slideways 12 when these slide bases 15 are slid to predetermined positions. Moreover, a grasping member 19 penetrates through the grasping arm 16. A hole 18 is formed on each grasping arm 16 corresponding to a place where the grasping member 19 has been passed, wherein an anti-loosing member 20 is screwed into the hole 18 respectively on two opposite sides of the hole 18 for locking up these grasping members 19 to prevent them from loosing when they are extended downward to predetermined positions.

In addition, a man-machine interface 30 and its related operation buttons 31 are provided on one side of the machine body 1. By means of a machine-actuated screen and these operation buttons 31 on the man-machine interface 30, it is able to assign the transmission control box 2 to an action mode, control and choose the action mode to make a round-trip test or a unilateral test (the former is to test the clockwise and counterclockwise rotations, the latter is to test the unidirectional rotation), or assign parameter settings such as values of rotation rate (the rotation rate is set to rotation number per minute), sway angle (zero degree through 360 degree), retention time between sways (unit: second), action number (a round-trip sway indicates one time), and dot adjustment (it is applied to set the direction of off-center sway, wherein the positive value indicates that the off-center sway is in a clockwise direction and the negative value indicates that the off-center sway is in a counterclockwise direction). As a result, the support platform 11 performs the related and required tests and its rotation is provided with more variations.

Figure 2:
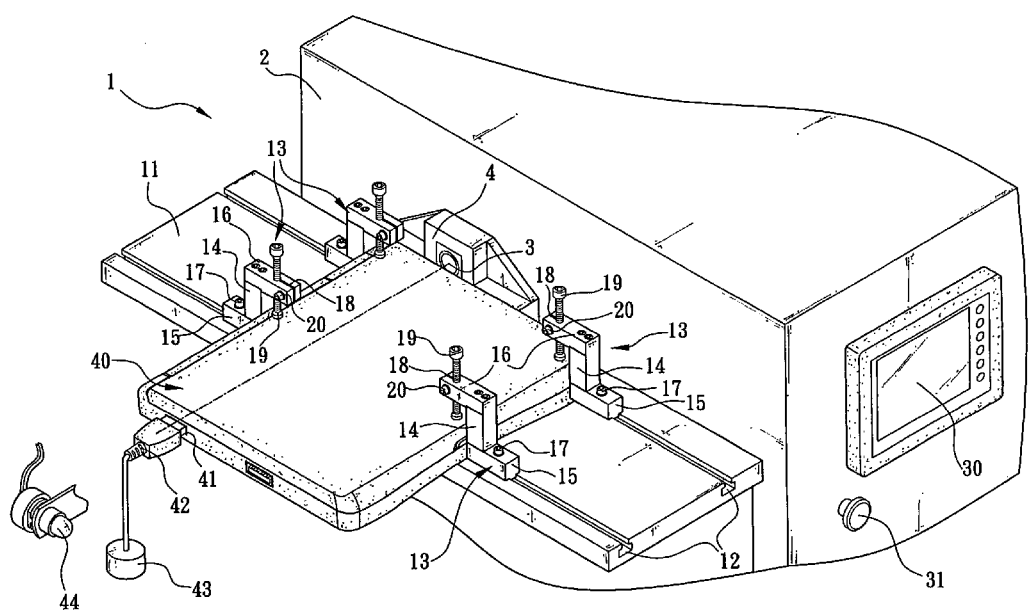
FIG. 2 is a schematic view showing the test status of the present invention that fixes a notebook computer on a support platform of a machine body.

According to the aforementioned components, it is apparent that when load rotation lifetimes of a long side and a short side of a connection port on an electronic apparatus is to be tested, as shown in FIG. 2, a connection port 41 of a notebook computer 40 is adopted as a testing object in accordance with a preferred embodiment of the present invention. First, the notebook computer 40 is put on the support platform 11 to enable the connection port 41 of the notebook computer 40, which desires to be tested, to align exactly with the rotation shaft 3. Next, these grasping components 13 push against both side surfaces of the notebook computer 40 along these slideways 12 (as shown in FIG. 1). Next, these slide bases 15 are moved against both side surfaces of the notebook computer 40 to prevent it from moving by adjusting these regulating buttons 17. At this moment, these grasping members 19 are shifted downward to press exactly on one surface of the notebook computer 40 and the anti-loosing members 20 are applied to lock these grasping members 19 to prevent them from loosing. As a result, the notebook computer 40 is capable of being firmly fixed onto the support platform 11. Moreover, a load connector 42 is plugged into the connection port 41, wherein a replaceable load object 43 is mounted on the other end of the load connector 42 and a sensor 44 is mounted in a position corresponding to the load object 43 for the purpose of transmitting test signal.

Figure 3:
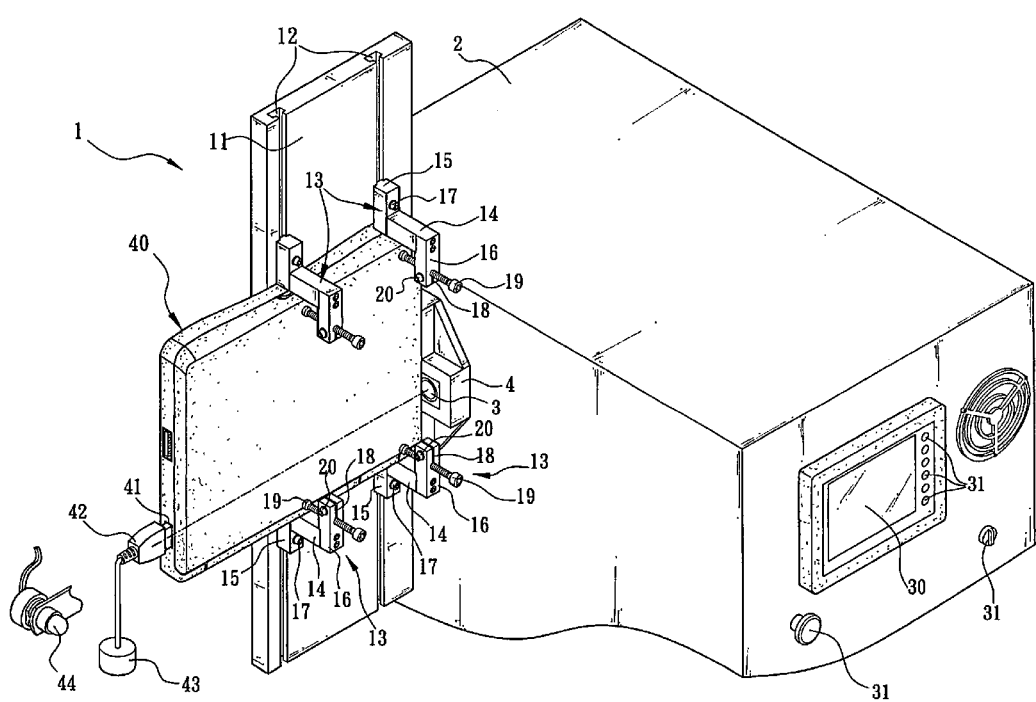
FIG. 3 is a schematic view showing another test status of the present invention that fixes a notebook computer on a support platform of a machine body.

Before performing the test, the related parameters settings, for example, dot adjustment, rotation rate, sway angle, action number, retention time, etc, can be set by means of the operation buttons 31 and the machine-actuated screen on the man-machine interface 30. Next, the action mode of the machine body 1 is set to make a round-trip test or a unilateral test. In this preferred embodiment, the machine body 1 is set to make a round-trip test. Finally, the machine body 1 is actuated, wherein an initial test status is shown in FIG. 2, which shows the test status of two long sides of the connection 41 that bears a vertical force. After the retention time reaches a predetermined time, which is preset in the parameter setting, the support platform 11 will be rotated in an angle according to the preset sway angle in the parameter setting. Referring to FIG. 3 of this preferred embodiment, which shows the test status of two short sides of the connection 41 that bears a vertical force. If the retention time reaches a predetermined time, which is preset in the parameter setting, the support platform 11 will be rotated back to its original state (as shown in FIG. 2) since the action mode of this preferred embodiment is set to make the round-trip test. Moreover, the action number of the support platform 11 will count this action in, and the support platform 11 repeats the previous action until the counted action number reaches a predetermined number, which is preset in the parameter setting. However, if the load object 43 falls down during the test, the sensor 44 will transmit a signal to the machine body 1. Since the action number does not reach the predetermined number of the setting, the machine body 1 will stop the test automatically. As a result, load rotation lifetime of the connection port 41 will be acquired by merely replacing with various load objects 43 to perform tests.

While the invention has been described by means of specific embodiments, numerous modifications and variations could be made thereto by those skilled in the art without departing from the scope and spirit of the invention set forth in the claims.

What is claimed is:

1. A test mechanism for testing a connection port of an electronic apparatus comprising:
   a machine body having a transmission control box inside and a rotation shaft extended from the transmission control box; and
   a support platform connected to the rotation shaft and driven by the rotation shaft, wherein at least a slideway is disposed on the support platform and two mobile grasping components are mounted respectively on the slideways;
   an electronic apparatus firmly fixed onto the support platform by means of the grasping components, wherein at least one connection port mounted on one side of the electronic apparatus is capable of connecting with a load object; and
   a sensor mounted in a position corresponding to the load object for transmitting a test signal to stop the test mechanism from performing experiment if the load object falls.

2. The test mechanism of claim 1 wherein each one of the grasping components comprises a main body, a slide base provided on one end of the main body being slidablely inserted in the slideway, an adjusting button disposed on the slide base, a grasping arm provided on the other end of the main body, a grasping member penetrated through the grasping arm, and a hole formed on the grasping arm corresponding to a position where the grasping member has been passed, wherein the slide base and the grasping arm are arranged in opposite directions and an anti-loosing member is screwed into the hole.

3. The test mechanism of claim 1 wherein the support platform utilizes a connection piece that mounts on one end of the support platform to connect with the rotation shaft so as to enable the rotation shaft to drive the connection piece for driving and rotating the support platform.

4. The test mechanism of claim 1 wherein the support platform is disposed on the rotation shaft adjacent to the transmission control box in a position eccentric to the rotation shaft.

5. The test mechanism of claim 1 wherein the connection port aligns exactly with the rotation shaft when the electronic apparatus is firmly fixed onto the support platform.

6. The test mechanism of claim 1 wherein a man-machine interface and its related operation buttons are provided on one side surface of the machine body such that it is able to input a signal by means of the man-machine interface and its related operation buttons to enable the support platform to perform related and required tests.

* * * * *